United States Patent
Orr et al.

(10) Patent No.: US 10,117,599 B2
(45) Date of Patent: Nov. 6, 2018

(54) SUBJECT INTERFACE APPLIANCE AND METHOD FOR DELIVERING A BREATHABLE SUBSTANCE TO A SUBJECT WHILE OBTAINING GAS SAMPLES FROM THE AIRWAY OF THE SUBJECT

(75) Inventors: Joseph Allen Orr, Park City, UT (US); Soeren Hoehne, Salt Lake City, UT (US); Lara Brewer, Bountiful, UT (US)

(73) Assignee: Koninklijke Philips N.V., Eindhoven (NL)

(*) Notice: Subject to any disclaimer, the term of this patent is extended or adjusted under 35 U.S.C. 154(b) by 1671 days.

(21) Appl. No.: 13/518,913

(22) PCT Filed: Dec. 10, 2010

(86) PCT No.: PCT/IB2010/055753
§ 371 (c)(1),
(2), (4) Date: Jun. 25, 2012

(87) PCT Pub. No.: WO2011/080641
PCT Pub. Date: Jul. 7, 2011

(65) Prior Publication Data
US 2013/0131533 A1    May 23, 2013

Related U.S. Application Data

(60) Provisional application No. 61/290,404, filed on Dec. 28, 2009.

(51) Int. Cl.
*A61M 16/06* (2006.01)
*A61B 5/097* (2006.01)
*A61M 16/08* (2006.01)

(52) U.S. Cl.
CPC .............. *A61B 5/097* (2013.01); *A61M 16/06* (2013.01); *A61M 16/0616* (2014.02);
(Continued)

(58) Field of Classification Search
CPC ............ A61M 16/0003; A61M 16/003; A61M 16/0033; A61M 16/0042; A61M 16/0605;
(Continued)

(56) References Cited

U.S. PATENT DOCUMENTS 4,263,908 A * 4/1981 Mizerak ................... 128/205.25
4,454,880 A * 6/1984 Muto et al. .............. 128/205.25
(Continued)

FOREIGN PATENT DOCUMENTS

| CN | 1409646 A | 4/2003 |
| JP | S6292802 A | 4/1987 |

*Primary Examiner* — LaToya M Louis

(57) ABSTRACT

A subject interface appliance (10) configured to deliver a breathable substance to a subject. The subject interface appliance includes a primary interface (12) configured to deliver a breathable substance to the subject, and a secondary interface (14) configured to obtain gas samples from the airway of the subject. The secondary interface is resiliently held at a default position with respect to the primary interface. The default position is located such that installation of the primary and secondary interfaces on the subject results in the application of a bias force to the secondary interface that holds the secondary interface in place.

10 Claims, 3 Drawing Sheets

(52) U.S. Cl.
CPC ...... *A61M 16/0666* (2013.01); *A61M 16/085* (2014.02); *A61M 16/0683* (2013.01); *A61M 2205/0216* (2013.01); *A61M 2210/0618* (2013.01); *A61M 2210/0625* (2013.01); *A61M 2230/43* (2013.01)

(58) Field of Classification Search
CPC .......... A61M 16/0666; A61M 16/0672; A61M 16/0677; A61M 16/0683; A61M 16/0841; A61M 16/0858; A61M 2016/103
See application file for complete search history.

(56) References Cited

U.S. PATENT DOCUMENTS

| | | | |
|---|---|---|---|
| 5,005,571 A * | 4/1991 | Dietz | 128/205.25 |
| 5,233,978 A * | 8/1993 | Callaway | 128/205.25 |
| 7,305,988 B2 * | 12/2007 | Acker et al. | 128/204.18 |
| 2002/0122746 A1 | 9/2002 | Yamamori | |
| 2004/0134498 A1* | 7/2004 | Strickland et al. | 128/207.18 |
| 2006/0249160 A1 | 11/2006 | Scarberry | |
| 2008/0319334 A1 | 12/2008 | Yamamori | |

\* cited by examiner

SUBJECT INTERFACE APPLIANCE AND METHOD FOR DELIVERING A BREATHABLE SUBSTANCE TO A SUBJECT WHILE OBTAINING GAS SAMPLES FROM THE AIRWAY OF THE SUBJECT

BACKGROUND OF THE INVENTION

1. Field of the Invention

The invention relates to interface appliances for delivering a breathable substance to a subject while obtaining samples of gas at or near the airway of the subject for monitoring.

2. Description of the Related Art

Subject interface appliances configured to support breathable substances for therapeutic purposes are known. Conventional use of these appliances includes using a primary interface appliance configured to deliver the breathable substance and a separate secondary interface appliance configured to obtain gas samples from gas exhaled from the airway of the subject. These primary and secondary interface appliances are generally formed as separate interface appliances that are used together in some therapeutic settings. Installing both the primary and secondary interface appliance on the face of a subject may be difficult due to mechanical interference between the two interface appliances (and/or the mechanisms that hold these appliances in place), and/or due to isolation of the secondary interface appliance from a user by the primary interface appliance.

SUMMARY OF THE INVENTION

One aspect of the invention relates to a subject interface appliance configured to deliver a breathable substance to the airway of a subject. In one embodiment, the subject interface appliance comprises a primary interface, a secondary interface, and a resilient member. The primary interface includes a mask barrier that encloses one or more external orifices of the airway of a subject including a first external orifice, and is shaped to form a delivery opening through which a breathable substance can be communicated to the one or more external orifices of the subject that are enclosed by the mask barrier. The secondary interface comprises a hollow prong and a main conduit. The hollow prong has a first end and a second end, and is configured to be inserted into the first external orifice of the airway of the subject such that the first end of the hollow prong is positioned inside of the first external orifice and the second end of the hollow prong is positioned outside of the first external orifice. The main conduit is connected to the hollow prong at or near the second end to receive gas that has entered the first end of the hollow prong within the airway of the subject, and is configured to guide the received gas toward a sensor configured to sample the gas received into the secondary interface through the hollow prong. The resilient member extends from the primary interface to the secondary interface, and is configured to hold the secondary interface spatially apart from the mask barrier at a default position with respect to the primary interface such that displacement of the secondary interface from the default position results in the application of a bias force by the resilient member on the secondary interface toward the default position. The interface appliance is configured such that if the primary interface is installed on the face of the subject the resilient member resiliently holds the hollow prong in place on the face of the subject with the first end of the hollow prong inside of the first external orifice of the airway of the subject.

Another aspect of the invention relates to a method of obtaining a sample of gas from the airway of a subject. In one embodiment, the method comprises engaging a first external orifice of the airway of a subject by a subject interface appliance, the secondary interface comprising a hollow prong having a first end and a second end, and being inserted into the first external orifice of the airway of the subject such that the first end of the hollowing prong is positioned inside of the first external orifice to engage the first external orifice of the airway of the subject, and the second end of the hollow prong is positioned outside of the first external orifice, and a main conduit connected to the hollow prong at or near the second end to receive gas that has entered the first end of the hollow prong within the airway of the subject, and being configured to guide the received gas toward a sensor configured to sample the gas received into the secondary interface through the hollow prong; enclosing one or more external orifices of the airway of the subject, including the first external orifice of the airway, wherein the one or more external orifices of the airway of the subject are enclosed by a primary interface of the subject interface appliance, the primary interface including a mask barrier that encloses the one or more external orifices of the airway, wherein the mask barrier is shaped to form a delivery opening through which a breathable substance can be communicated to the one or more external orifices of the subject that are enclosed by the mask barrier; and applying a resilient bias force to the secondary interface that maintains the engagement between the secondary interface and the first external orifice of the airway of the subject, wherein the resilient bias force is applied to the secondary interface by a resilient member extending from the primary interface to the secondary interface.

Yet another aspect of the invention relates to a subject interface appliance configured to deliver a breathable substance to the airway of a subject. The subject interface appliance comprising means for enclosing one or more external orifices of the airway of a subject including a first external orifice, wherein the means for enclosing forms a delivery opening through which a breathable substance can be communicated to the one or more external orifices of the subject that are enclosed; means for obtaining gas from the airway of the subject comprising means for engaging the first external orifice of the airway of the subject, the means for engaging the first external orifice being configured to be inserted into the first external orifice of the airway of the subject such that a first end of the means for engaging the first external orifice is positioned inside of the first external orifice, and means for guiding the received gas toward a sensor configured to sample the gas received into the secondary interface through the means for engaging; and means for holding the means for obtaining gas from the airway of the subject spatially apart from the means for enclosing at a default position with respect to the means for enclosing such that displacement of the means for obtaining gas from the airway of the subject from the default position results in the application of a bias force by the means for holding on the means for obtaining gas from the airway of the subject toward the default position, wherein the means for holding resiliently holds the means for obtaining gas from the airway of the subject in place on the face of the subject with the means for engaging the first external orifice positioned inside of the first external orifice of the airway of the subject These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
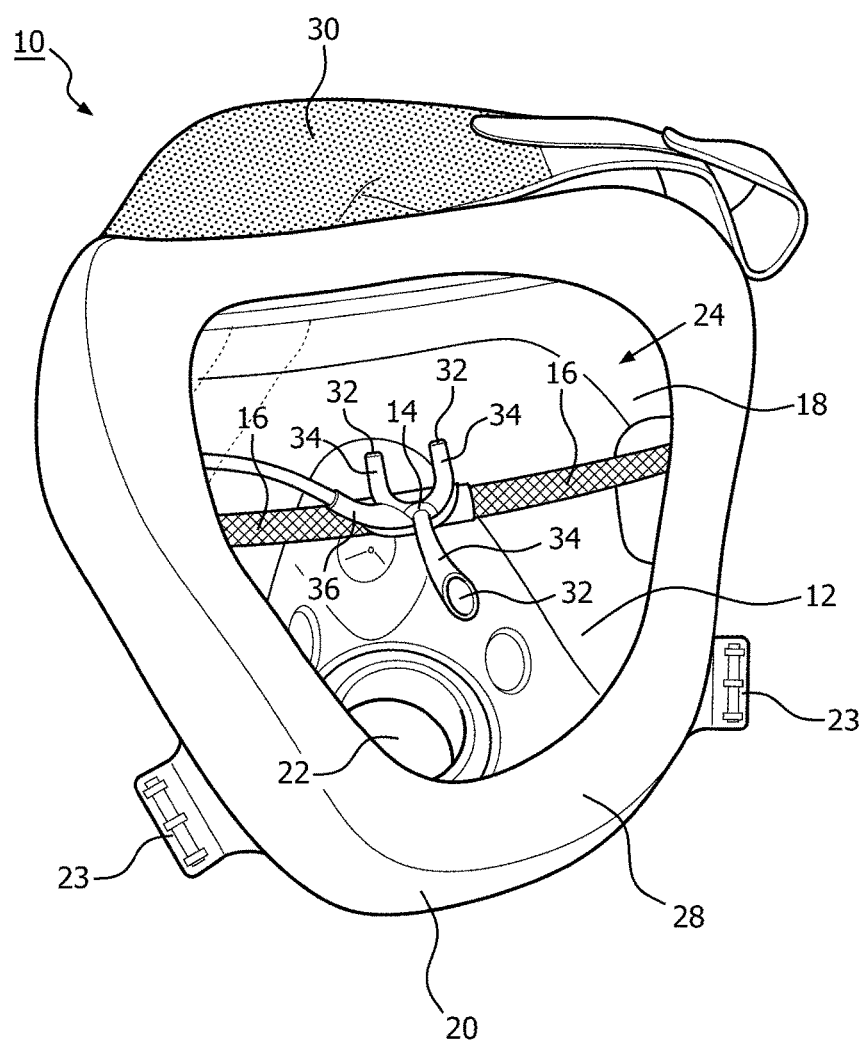
FIG. 1 illustrates a subject interface appliance configured to deliver a breathable substance to the airway of a subject, according to one or more embodiments of the invention.
Figure 2:
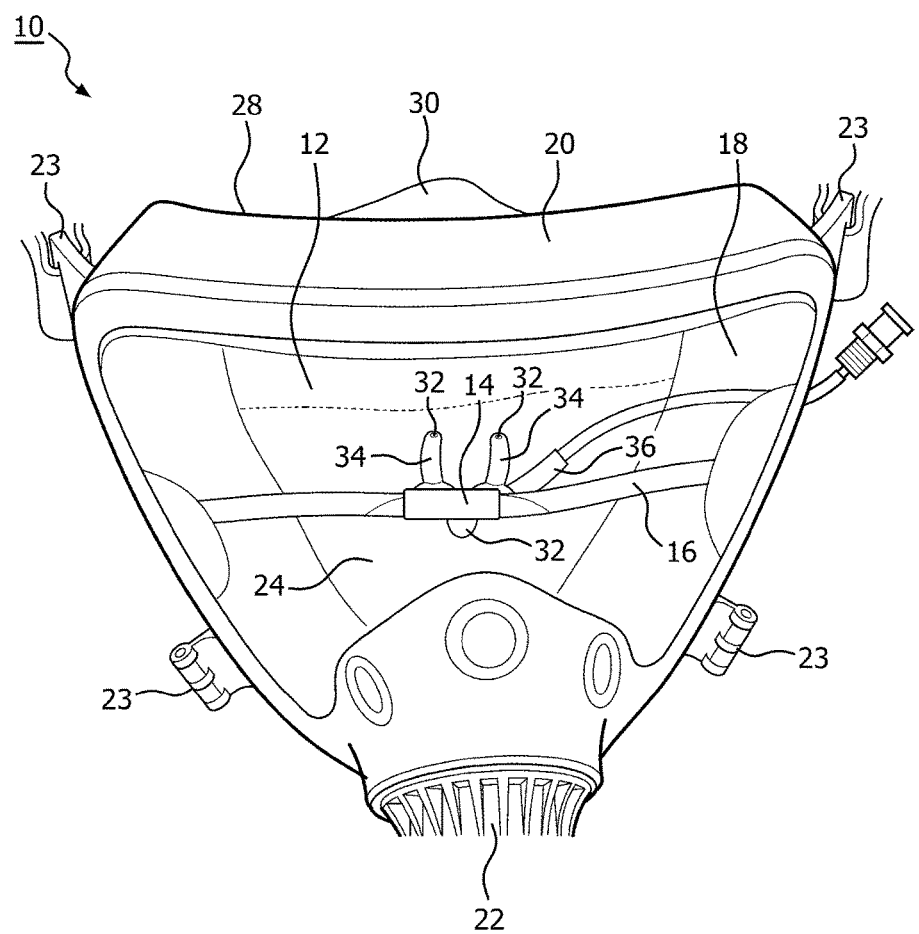
FIG. 2 illustrates a subject interface appliance configured to deliver a breathable substance to the airway of a subject, according to one or more embodiments of the invention.

FIGS. 1 and 2 illustrates a subject interface appliance 10 configured to deliver a breathable substance to the airway of a subject. For example, in one embodiment subject interface appliance 10 is used to deliver a flow of breathable gas to the airway of the subject. The flow of breathable gas may be delivered in accordance with a pressure support therapy regime, have a specific composition (e.g., elevated oxygen), and/or may be delivered to provide other therapeutic benefits. The subject interface appliance 10 is further configured to obtain samples of gas from the airway of the subject so that one or more parameters of the gas exhaled from the lungs of the subject can be monitored. For example, the samples of gas obtained by subject interface appliance 10 may be implemented to detect the composition of the gas samples (e.g., the partial pressure and/or concentration of one or more molecular species). In one embodiment, subject interface appliance 10 includes a primary interface 12, a secondary interface 14, and one or more resilient members 16.

The primary interface 12 is configured to deliver a breathable substance to the airway of the subject. The breathable substance is received by primary interface 12 from a source. By way of non-limiting example, the source may include a pressure support device configured to provide pressure support therapy, a ventilator configured to provide non-invasive ventilation, a source of gas having a specific composition (e.g., oxygen-enriched gas), and/or other sources configured to generate and/or provide a flow of breathable gas. The primary interface 12 includes a mask barrier 18, a seal portion 20, a source connector 22, one or more headgear connectors 23, and/or other components.

The mask barrier 18 is configured to enclose one or more external orifices of the airway of the subject. The one or more external orifices may include one or both of the nares of the subject and/or the mouth of the subject. The mask barrier 18 is formed generally as a membrane having a generally domed shape that defines a delivery opening 24 through which a breathable substance is communicated with the airway of the subject. When installed on the face of the subject, the mask barrier 18 acts as a barrier between a space surrounding the one or more external orifices of the airway of the subject and ambient atmosphere. A flow path is created in this space by primary interface 12 between source connector 22 and delivery opening 24. The mask barrier 18 may be formed from polycarbonate and/or other materials.

The seal portion 20 is configured to form a sealed (or substantially sealed) engagement between primary interface 12 and the face of the subject surrounding the one or more external orifices of the airway of the subject. The seal portion 20 is disposed on primary interface 12 at the edge of delivery opening 24. The seal portion may be formed from a resilient material, such as an elastomeric polymer, plastic, and/or other resilient materials, to enhance the seal formed between the face of the subject and seal portion 20. The seal between seal portion 20 and the face of the subject may be enhanced by a seal surface 28 formed by seal portion 20 that is configured to increase the surface area over which physical contact is made between seal portion 20 and the face. In one embodiment, seal portion 20 is connected to or mounted on a lip formed by mask barrier 18 along the edge of delivery opening 24. This connection or mounting may be removable, or substantially fixed.

The source connector 22 is configured to removably couple primary interface 12 with a source that provides a breathable substance to subject interface appliance 10. The source may include, for example, a pressure support device, a ventilator, a wall gas source, a Dewar, and/or other sources of breathable substances. The breathable substance may be a flow of breathable gas. In one embodiment, source connector 22 is a conduit with a first end that is configured to be releasably engaged with a source (or a respiratory circuit that couples source connector 22 to the source), and a second end that communicates with the interior of mask barrier 18.

The headgear connectors 23 are mounted on the exterior of mask barrier 18, and are configured to connect subject interface appliance 10 with a headgear 30. In the embodiments illustrated in FIGS. 1 and 2, headgear connectors 23 are disposed at or near delivery opening 24 (e.g., adjacent to seal portion 20). The headgear 30 may include one or more straps, pads, rigid members, and/or other components configured to hold subject interface appliance 10 in place on the face of the subject. In the embodiments illustrated in FIGS. 1 and 2, headgear 30 includes straps that can be releasably connected to headgear connectors 23. The releasable connection between headgear 30 and a given headgear connector 23 may accomplished via a snap-fit, a press-fit, a friction-fit, hood-and-loop fasteners, a threaded fastener, and/or other mechanisms for holding a connection between two separate components. In one embodiment, headgear connectors 23 are connected to headgear 30 in a substantially non-releasable manner.

The secondary interface 14 is configured to obtain samples of gas from locations at or near the one or more external orifices of the airway of the subject. Specifically, secondary interface 14 forms one or more gas inlets 32 configured to be inserted into at least one of the external orifices of the airway of the subject enclosed by primary interface 12 to obtain gas samples therefrom. The secondary interface 14 may include one or more of at least one hollow prong 34, a main conduit 36, and/or other components.

The hollow prongs 34 have a first end and a second end. The gas inlets 32 are formed by the first ends of hollow prongs 34. The hollow prongs 34 are configured to be inserted into external orifices of the airway of the subject such that the first ends are positioned within the external orifices of the airway to receive gas from the airway of the subject therein. The hollow prongs 34 may be formed from a relatively soft and/or resilient material to enhance the comfort of the subject. For example, hollow prongs 34 may be formed from elastomeric polymer material(s) and/or other materials.

In the embodiments illustrated in FIGS. 1 and 2, secondary interface 14 includes separate hollow prongs 34 for each of the nares and the mouth of the subject. This is not intended to be limiting. For instance, hollow prongs 34 may include fewer of hollow prongs 34, and may not obtain gas samples from the mouth of the subject and/or one of the nares of the subject. Further, in one embodiment, not all of hollow prongs 34 are configured to obtain gas samples. In this embodiment, one or more of hollow prongs 34 may be used to deliver a supplemental flow of gas for therapeutic purposes. For example, one of the hollow prongs 34 configured to be inserted into the nares of the subject may be used to deliver a flow of oxygen-enriched gas while the other hollow prongs 34 are used to obtain samples of gas from the airway of the subject for monitoring by the sensor.

In one embodiment, secondary interface 14 does not include all of the hollow prongs 34 shown in FIGS. 1 and 2. For example, a secondary interface including only gas inlets 32 for the nares, only for mouth, or only for a single nare, and/or other configurations also falls within the scope of this disclosure.

The main conduit 36 is connected to hollow prongs 34 at or near the second ends of hollow prongs 34. The main conduit 36 is configured to receive gas that has entered secondary interface 14 through hollow prongs 34, and to guide the received gas toward a sensor. The sensor (not shown) may be configured to generate an output signal conveying information related to one or more parameters of the gas sampled by secondary interface 14 at or near the airway of the subject. For example, the one or more parameters may include a composition of the gas received by secondary interface 14, and/or other parameters.

The sensor to which main conduit 36 conveys the received gas may be located outside of primary interface 12. As such, in one embodiment, primary interface 12 is configured to enable main conduit 36 to pass through primary interface 12. For example, main conduit 36 may run through mask barrier 18. The mask barrier 18 is configured to maintain a seal around main conduit 36 at the point where main conduit 36 passes through mask barrier 18 to prevent leakage between the interior and the exterior of mask barrier 18 at this point.

As can be seen in FIGS. 1 and 2, during operation secondary interface 14 is positioned within primary interface 12 to receive gas from the external orifices of the airway of the subject while a breathable substance is being delivered to the external orifices of the airway of the subject by primary interface 12. As such, in conventional interface appliances, the engagement between a secondary interface and the one or more external orifices of the subject is physically isolated from the exterior of a primary interface. This may cause the conventional interface appliance to be susceptible to the secondary interface becoming dislodged and/or insecure during use.

The resilient members 16 extend from primary interface 12 to secondary interface 14. The resilient members 16 are configured to hold secondary interface 14 spatially apart from mask barrier 18 at a default position with respect to primary interface 12. The resilient member 16 are formed at least in part from a resilient material such that displacement of secondary interface 14 from the default position results in the application of a bias force by resilient members 16 on secondary interface 14 toward its default position.

During use, the default position of secondary interface 14 with respect to primary interface 12 should be positioned such that if primary interface 12 is installed on the face of the subject the force applied to secondary interface 14 by resilient member 16 holds secondary interface 14 in place in the external orifices. By way of non limiting example, in FIGS. 1 and 2, if the default position of secondary interface 14 is in (or near) the a plane defined by seal portion 20, and is slightly higher than the nares of the subject, when subject interface appliance 10 is installed on the face of the subject, the bias applied to secondary interface 14 by resilient member 16 will secure the hollow prongs 34 that correspond to the nares of the subject in place in the nares. The resilient member 16 may be configured such that spring constant of the bias force applied holds hollow prongs 34 securely in place without being so tight that the subject experiences discomfort.

In one embodiment, resilient member 16 is adjustable such that the default position of secondary interface 14 can be customized for the face of the subject and/or the comfort of the subject. This may include moving the default position of secondary interface 14 up-down, left-right, toward-away from the face of the subject, and/or otherwise adjusted. By way of non-limiting example, if resilient member 16 includes one or more pieces of elastic material that suspend secondary interface 14 in place with respect to primary interface 12 (as shown in FIGS. 1 and 2), the connection(s) between secondary interface 14 and primary interface 12 may be adjustable. In one embodiment, the shape of resilient member 16 may be adjustable to customize the location of the default position of secondary interface 14.

It will be appreciated that although resilient member 16 is illustrated in FIGS. 1 and 2 as being formed entirely from a resilient material (e.g., elastic), this is not intended to be limiting. For example, resilient member 16 may include a rigid portion and a resilient portion. In one embodiment, the connection between primary interface 12 and resilient member 16 may be formed from a resilient material, and the portion of resilient member 16 extending from this connection to secondary interface 14 may be formed from a rigid material. Further, although resilient member 16 is illustrated in FIGS. 1 and 2 as connecting to primary interface 12 at two points on primary interface 12 at or near seal portion 20, this is not intended to be limiting. In one embodiment resilient member 16 only connects to primary interface 12 at one location. In one embodiment, resilient member 16 connects to primary interface 12 at more than two locations. In one embodiment, resilient member 16 connects to primary interface 12 at a position on or near mask barrier 18 that is remote from seal portion 20 (e.g., near source connector 22).

Figure 3:
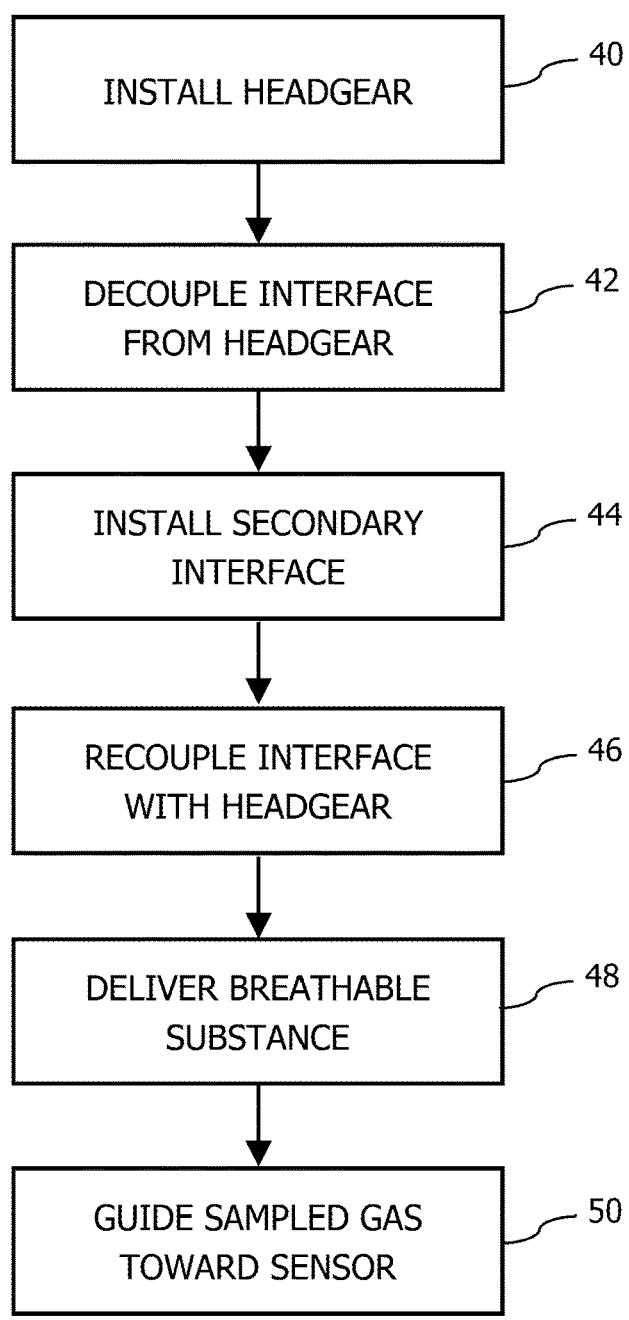
FIG. 3 is a flow chart of a method, according to one or more embodiments of the invention.

The following is a description of how subject interface appliance 10 may be installed on the face of a subject. It will be appreciated that this exemplary method for installing subject interface appliance 10 in the face of the subject is only provided for illustrative purposes, and does not limit the scope of this disclosure. FIG. 3 provides a flow chart of a method 38 including at least some of the operations involved in the installation process.

At an operation 40, a headgear that will hold the subject interface appliance in place on the face of the subject is placed on the head of the subject. To ensure that the headgear is adjusted appropriately, the subject interface appliance may be connected to the headgear while the head gear is placed on the head of the subject. At operation 40, particular attention is paid to the fit of a primary interface of the subject interface appliance with respect to the face of the subject. In one embodiment, the primary interface is similar to or the same as primary interface 12 (shown in FIGS. 1 and 2 and described above). In one embodiment, the headgear is similar to or the same as headgear 30 (shown in FIGS. 1 and 2 and described above).

At an operation 42, the subject interface appliance is decoupled from the headgear, leaving the headgear installed on the head of the subject. This may include decoupling headgear from headgear connectors disposed on the subject interface appliance. In one embodiment, the headgear connectors similar to or the same as headgear connectors 23 (shown in FIGS. 1 and 2 and described above).

At an operation 44, a secondary interface of subject interface appliance is positioned on the face of the subject such that the secondary interface engages one or more external orifices of the subject such that the secondary interface can obtain samples of gas at or near the one or more external orifices of the airway of the subject. For example, the secondary interface may be configured to provide one or more gas inlets that should be positioned at or within the one or more external orifices of the airway of the subject. In one embodiment, the secondary interface is similar to or the same as secondary interface 14 (shown in FIGS. 1 and 2 and described above).

At an operation 46, the primary interface is re-installed on the face of the subject. This includes recoupling the primary interface with the headgear such that the headgear holds the primary interface in place on the face of the subject to enclose one or more external orifices of the airway of the subject, including the one or more external orifices in which the secondary interface is installed.

The primary interface and the secondary interface are connected to each other by a resilient member. The resilient member resiliently holds the secondary interface at a default position with respect to the primary interface. The default position of the secondary interface is configured such that if the primary interface is installed on the face of the subject (e.g., at operation 46), the secondary interface is moved away from the default position, thereby causing the resilient member to apply a resilient bias force to the secondary interface that holds the gas inlets of the secondary interface in place in the one or more external orifices of the airway of the subject.

At an operation 48, a breathable substance is delivered to the subject through the subject interface appliance. In one embodiment, the breathable substance is delivered to the subject through the primary interface.

At an operation 50, gas samples obtained at or near the one or more external orifices of the subject are guided to a sensor that monitors one or more parameters of the gas. In one embodiment, operation 50 is performed by the secondary interface.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A subject interface appliance configured to deliver a breathable substance to the airway of a subject, the subject interface appliance comprising:
  a primary interface including a mask barrier that encloses one or more external orifices of the airway of a subject including a first external orifice, wherein the mask barrier is shaped to form a delivery opening through which a breathable substance can be communicated to the one or more external orifices of the subject that are enclosed by the mask barrier;
  a secondary interface, the secondary interface comprising:
    a hollow prong having a first end and a second end, the hollow prong being configured to be inserted into the first external orifice of the airway of the subject such that the first end of the hollow prong is positioned inside of the first external orifice and the second end of the hollow prong is positioned outside of the first external orifice, and
    a main conduit connected to the hollow prong at or near the second end to receive gas that has entered the first end of the hollow prong within the airway of the subject, the main conduit being configured to guide the received gas toward a sensor configured to generate an output signal conveying information related to one or more parameters of the received gas received by the secondary interface through the hollow prong; and
  a resilient member extending from the primary interface to the secondary interface, the resilient member being configured to suspend and hold the secondary interface spatially apart from the mask barrier within the delivery opening of the primary interface at a default position near a plane defined by a seal portion with respect to the primary interface such that displacement of the secondary interface from the default position, in response to installation of the primary interface to enclose the one or more external orifices of the airway of the subject, results in the application of a bias force by the resilient member on the secondary interface toward the default position, wherein the interface appliance is configured such that responsive to the primary interface being installed on a face of the subject, the resilient member resiliently biases the hollow prong in place on the face of the subject with the first end of the hollow prong inside of the first external orifice of the airway of the subject,
  wherein the resilient member is configured to adjust the bias force such that the default position of the secondary interface is customizable to the subject.

2. The subject interface appliance of claim 1, wherein the primary interface further comprises the seal portion formed around a peripheral edge of the mask barrier around the delivery opening, the seal portion being configured to engage the face of the subject in a substantially sealed engagement between the primary interface and the face of the subject.

3. The subject interface appliance of claim 2, wherein the resilient member extends between the secondary interface and opposing sides of the primary interface at or near the seal portion of the primary interface.

4. The subject interface appliance of claim 1, wherein the primary interface further comprises a source connector configured to removably couple the primary interface with a source of the breathable substance such that the breathable substance is delivered to at least the first external orifice of the airway of the subject through the source connector and the delivery opening.

5. The subject interface appliance of claim 1, wherein the resilient member is elongated and defines opposite ends, the resilient member opposite ends being connected with the mask barrier adjacent opposite sides of the mask barrier.

6. A method of obtaining a sample of gas from the airway of a subject, the method comprising:

engaging a first external orifice of the airway of a subject, wherein the first external orifice of the airway is engaged by a secondary interface of a subject interface appliance, the secondary interface comprising:

a hollow prong having a first end and a second end, the hollow prong being inserted into the first external orifice of the airway of the subject such that the first end of the hollowing prong is positioned inside of the first external orifice to engage the first external orifice of the airway of the subject, and the second end of the hollow prong is positioned outside of the first external orifice, and a main conduit connected to the hollow prong at or near the second end to receive gas that has entered the first end of the hollow prong within the airway of the subject, the main conduit being configured to guide the received gas toward a sensor configured to generate an output signal conveying information related to one or more parameters of the received gas received by the secondary interface through the hollow prong;

enclosing one or more external orifices of the airway of the subject, including the first external orifice of the airway, wherein the one or more external orifices of the airway of the subject are enclosed by a primary interface of the subject interface appliance, the primary interface including a mask barrier that encloses the one or more external orifices of the airway, wherein the mask barrier is shaped to form a delivery opening through which a breathable substance can be communicated to the one or more external orifices of the subject that are enclosed by the mask barrier;

applying a resilient bias force to the secondary interface that maintains the engagement between the secondary interface and the first external orifice of the airway of the subject, wherein the resilient bias force is applied to the secondary interface by a resilient member extending from the primary interface to the secondary interface, the resilient member being configured to suspend and hold the secondary interface spatially apart from the mask barrier within the delivery opening of the primary interface at a default position near a plane defined by a seal portion with respect to the primary interface such that displacement of the secondary interface from the default position, in response to installation of the primary interface to enclose the one or more external orifices of the airway of the subject, results in the application of the resilient bias force by the resilient member on the secondary interface toward the default position, wherein the interface appliance is configured such that responsive to the primary interface being installed on a face of the subject, the resilient member resiliently biases the hollow prong to hold the hollow prong in place on the face of the subject with the first end of the hollow prong inside of the first external orifice of the airway of the subject; and adjusting the resilient bias force applied by the resilient member to customize the engaging between the secondary interface and the first external orifice of the airway of the subject.

7. The method of claim 6, further comprising forming a seal between the face of the subject and the primary interface around an edge of the mask barrier.

8. The method of claim 7, wherein the resilient member includes an elongated portion connected at opposite ends to opposite sides of the primary interface at or near the seal between the primary interface and the face of the subject.

9. The method of claim 6, further comprising delivering the breathable substance to the first orifice of the airway of the subject through the delivery opening.

10. The subject interface appliance of claim 1, wherein the secondary interface is supported only by the resilient member and the resilient member is supported by the mask barrier.

* * * * *